United States Patent [19]

Hotta et al.

[11] Patent Number: 5,672,723

[45] Date of Patent: Sep. 30, 1997

[54] PROCESS FOR PREPARATION OF 1-ACYL-2-SUBSTITUTED HYDRAZINES

[75] Inventors: Hiroki Hotta, Yono; Hiroyasu Sugizaki, Tokyo; Tetsuya Toya, Yono; Mikio Yanagi, Okegawa, all of Japan

[73] Assignees: Nippon Kayaku Kabushiki Kaisha; Sankyo Company, Limited, both of Tokyo, Japan

[21] Appl. No.: 604,679

[22] Filed: Feb. 21, 1996

Related U.S. Application Data

[63] Continuation of Ser. No. 276,288, Jul. 18, 1994, abandoned.

[30] Foreign Application Priority Data

Jul. 20, 1993 [JP] Japan ..................... 5-199974

[51] Int. Cl.$^6$ .................. C07D 311/04; C07C 241/02
[52] U.S. Cl. .................. 549/402; 549/362; 549/398; 549/405; 564/148; 564/149; 564/150
[58] Field of Search ..................... 564/148, 149, 564/150; 549/405, 398, 402, 362

[56] References Cited

U.S. PATENT DOCUMENTS 4,814,349  3/1989  Addor et al. ..................... 514/522

FOREIGN PATENT DOCUMENTS

| 0 228 564 | 7/1987 | European Pat. Off. . |
| 0 232 075 | 8/1987 | European Pat. Off. . |
| 0 236 618 | 9/1987 | European Pat. Off. . |
| 0 286 746 | 10/1988 | European Pat. Off. . |
| 0 496 342 | 7/1992 | European Pat. Off. . |
| 4-290856 | 10/1992 | Japan . |

OTHER PUBLICATIONS

J. Heterocyl. Chem. vol. 14, No. 7, 1977 pp. 1147–1150, N.P. Peet and S. Sunder 'Synthesis of 3-M ethyl-[1,2,4]-triazepino[6,5,4,-jk]carbazol-4(3H)one'.

J. Indian Chem. Soc. vol. 64, o. 2, 1987 pp. 122–124, M.H. Jagdale et al., 'Kinetics and Mechanism of Acid Hydrolysis of Nitrobenzoic Acid Hydrazides'.

*Primary Examiner*—Shailendra Kumar
*Attorney, Agent, or Firm*—Nields & Lemack

[57] ABSTRACT

The present invention can provide a process for the preparation of an 1-acyl-2-substituted hydrazine compound from a mixture containing the 1-acyl-2-substituted hydrazine and an 1-acyl-1-substituted hydrazine by selective hydrolysis or alcoholysis of the 1-acyl-yl-1-substituted hydrazine in the presence of an acid catalyst, and by separation of the resulting carboxylic acid and derivative thereof.

The 1-acyl-2-alkyl hydrazine obtained has a high purity.

16 Claims, No Drawings

PROCESS FOR PREPARATION OF 1-ACYL-2-SUBSTITUTED HYDRAZINES

This application is a continuation of application Ser. No. 08/276,288 filed Jul. 18, 1994, now abandoned.

[APPLICATION FIELDS OF INVENTION]

The present invention relates to a process for the preparation of 1-acyl-2-alkyl hydrazines which are usable intermediates for the production of 1-alkyl-1,2-diacyl hydrazines which are known to have insecticidal activities.

[PRIOR ARTS]

As methods for the synthesis of monoacyl monoalkyl hydrazines, it is an usual one that acyl chlorides are condensed with alkyl hydrazines in the presence of bases.

in this hydrazide formation reaction with acyl chlorides, there is low regioselectivity for the nitrogen atom at 1- or 2-position. Therefore, the desired product, 1-acyl-2-alkyl hydrazine, may be obtained only in the form of a mixture of it and the by-product, 1-acyl-1-alkyl hydrazine.

For the selective preparation of 1-acyl-2-alkyl hydrazines, European Patent Nos. 236618, 232075 and 286746 describe a certain method wherein hydrazones are derived from acylhydrazines and then reduced.

Japanese Patent Application Laying Open (KOKAI) No. 4-290856 (1992) describes another method wherein the condensation is carried out using $ArCOCCl_3$ instead of the acyl chlorides to decrease the formation of 1-acyl-1-alkyl hydrazines.

For the selective preparation of 1-acyl-1-alkyl hydrazines, European Patent No. 228564 and U.S. Pat. No. 4,814,349 describe a method wherein hydrazones are derived from alkylhydrazines, acylated and then hydrolyzed.

[PROBLEMS TO BE SOLVED BY INVENTION]

The regioselectivity is important in acylation of hydrazines because they are difunctional molecules.

When monoacyl monoalkylhydrazines are prepared from acyl chlorides and monoalkylhydrazines, there are obtained mixtures of 1-acyl-2-alkylhydrazines and 1-acyl-1-alkylhydrazines and it is difficult to obtain 1-acyl-2-alkylhydrazines with high purities.

In addition, 1-acyl-2-tertiary-alkylhydrazines can not be prepared by the methods as described in the above-mentioned European Patents, wherein hydrazones are derived from hydrazines and then reduced.

The invention provides a process for preparing 1-acyl-2-alkylhydrazines with high purities by selective hydrolysis or alcoholysis of 1-acyl-1-alkylhydrazines which are by-produced.

[SUMMARY OF INVENTION]

The inventors have conducted intensive studies to overcome the problems above and found that, as described below, 1-acyl-1-alkylhydrazines represented by the general formula (2) may be easily changed to carboxylic derivatives of the general formula (3) in the presence of an acid catalyst under heating, while 1-acyl-2-alkylhydrazines represented by the general formula (1) are relatively stable under acidic conditions and then may hardly be subjected to hydrolysis or alcoholysis. Accordingly, we have completed the invention.

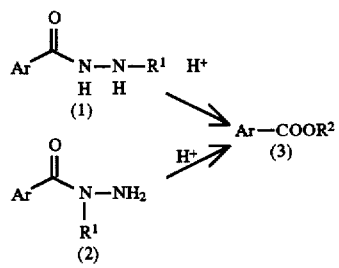

Wherein Ar is a phenyl or naphthyl ring substituted by 1 to 5 substituents independently selected from the group consisting of hydrogen, halogen, $(C_1-C_6)$ alkyl, $(C_1-C_6)$ alkoxy, halo $(C_{1-C6})$ alkyl and halo $(C_1-C_6)$alkoxy, or when two adjacent positions on the phenyl ring are substituted, these groups can form $—OCH_2CH_2O—$ or $—OCH_2CH_2CH_2—$, $R^1$ is an $(C_1-C_8)$alkyl group, and $R^2$ is hydrogen or an $(C_1-C_6)$alkyl. The process of the present invention is illustrated below. (In the formula, Ar, $R^1$ and $R^2$ are as described above.)

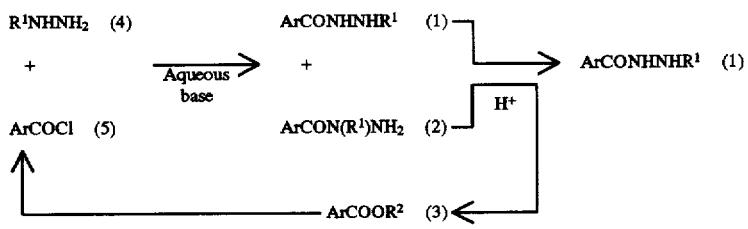

That is, the process for the preparation of an 1-acyl-2-substituted hydrazine compound represented by the general formula (1):

wherein Ar and $R^1$ are as described above, from a mixture comprising the hydrazine compound of the general formula (1) and an 1-acyl-1-substituted hydrazine represented by the general formula (2):

wherein Ar and $R^1$ are as described above, the mixture being prepared by condensing a monosubstituted hydrazine represented by the general formula (4):

$$R^1NH\text{—}NH_2 \quad (4)$$

wherein Ar and $R^1$ are as described above, with an acyl chloride derivative represented by the general formula (5):

$$Ar\text{—}COCl \quad (5)$$

wherein Ar is as described above, the process comprising the following steps of:

deriving a compound represented by the general formula (3):

$$Ar\text{—}COOR^2 \quad (3)$$

wherein Ar and $R^2$ are as described above, from the 1-acyl-1-substituted hydrazine of the general formula (2) by selective hydrolysis or by alcoholysis in the presence of an acid catalyst; and separating the compound represented by the general formula (3) therefrom to purify the hydrazine compound represented by the general formula (1), has been found.

[DETAILED DESCRIPTION OF INVENTION]

The invention may be carried out according to the following.

Mixtures comprising a compound of the general formula (1) and a compound of the general formula (2), used for the invention, may be obtained by reacting a monosubstituted hydrazine of the general formula (4) with an acyl chloride derivative of the general formula (5) in an inactive or substantially inactive solvent in the presence of a base.

Examples of the compounds of general formula (4), usable for the above-mentioned procedures, include t-amylhydrazine, isopropylhydrazine, t-butylhydrazine, neopentylhydrazine, α-methylneopentylhydrazine, isobutylhydrazine, isopentylhydrazine and isooctylhydrazine, preferably t-butylhydrazine.

Examples of the compounds of the general formula (5), usable for the above-mentioned procedures, include benzoyl chloride derivatives in which the phenyl group is substituted by hydrogen, halogen or $(C_1\text{–}C_6)$alkyl, such as benzoyl chloride, 4-chlorobenzoyl chloride, 4-methylbenzoyl chloride, 4-ethylbenzoyl chloride, 3,4-dichlorobenzoyl chloride, 2-bromobenzoyl chloride, 2,3-dimethylbenzoyl chloride, 3,5-dimethylbenzoyl chloride, 5-methylchroman-6-carboxylic chloride and 5-methyl-1,4-benzodioxane-6-carboxylic chloride. Preferable compounds may be 4-ethylbenzoyl chloride, 3,5-dimethylbenzoyl chloride, 5-methylchroman-6-carboxylic chloride and 5-methyl-1,4-benzodioxane-6-carboxylic chloride.

Examples of the solvents suitable for the use in the above-mentioned procedures include water; alcohols, such as methanol, ethanol and isopropanol; hydrocarbons, such as toluene, xylene, hexane and heptane; ethylene glycol dimethyl ether; tetrahydrofuran; acetonitrile; pyridine; haloalkanes such as methylene chloride and mixtures thereof, preferably water, toluene, methylene chloride and mixtures thereof.

The amount of the solvent used is 3 L or less, preferably 0.5 to 2 L per mole of the compound of the general formula (5).

Examples of the bases suitable for the use in the above-mentioned procedures include tertiary amines, such as triethylamine and pyridine, potassium carbonate, sodium carbonate, sodium hydroxide and potassium hydroxide, preferably sodium hydroxide, potassium hydroxide and triethylamine. The amount of the base used may be an equivalent or more, preferably one to three equivalents, relative to that of the compound used of the general formula (5).

The amount of the compound of the general formula (4) may be an equivalent or more relative to that of the compound of the general formula (5).

The reaction temperature may be about –20° C. to about 100° C., preferably –10° to 50° C.

The treatment using an acid as a catalyst according to the invention may be carried out by either Method (a) or (b) below.

Method (a)

A mixture of hydrazines of the general formulae (1) and (2) is heated and stirred in the presence of an acid as a catalyst, and accordingly a carboxylic derivative of the general formula (3) is formed due to the hydrolysis of 1-acyl-1-substituted hydrazine of the general formula (2). The 1-acyl-2-substituted hydrazine of the general formula (1) can be purified by the removal of the carboxylic derivative.

In this method, mixtures containing hydrazines of the general formulae (1) and (2) in any proportion can be applied. As reaction solvents, water may be preferably used mainly but mixtures of water and an alcohol, such as methanol, ethanol or isopropanol, or of water and an ether, such as tetrahydrofuran or dioxane may be preferably used also. In addition, mixtures of water and an organic solvent selected from the group consisting of aliphatic hydrocarbons, such as hexane and heptane, aromatic hydrocarbons, such as benzene, toluene and xylene, halogenated hydrocarbons, such as chloroform, dichloromethane and chlorobenzene and ketones, such as acetone and methylethyl ketone may be used as the reaction solvent. The amount of water used may be the theoretical or a large excess thereof. The amount of the reaction solvent used is not more than 10 L, preferably 0.5 to 5 L, per mole of the hydrazines mixture to be purified.

The reaction may be carried out at temperatures 10° C. to the boiling point of the reaction solvent, preferably about 50° C. to about 100° C.

The acid catalyst may include inorganic acids, such as hydrochloric acid, sulfuric acid and nitric acid, and organic acids, such as p-toluene sulfonic acid. The preferable acid may be an inorganic acid and more preferable one may be hydrochloric acid or sulfuric acid. The concentration of the acid used may be normally not more than 50% by weight, preferably not more than 30% by weight, most preferably 1 to 5% by weight, relative to the reaction solvent.

The carboxylic derivative of the general formula (3) may be separated and recovered by filtration or extraction. After the separation of the carboxylic derivative of the general formula (3), the 1-acyl-2-substituted hydrazine of the general formula (1) can be obtained in the form of salt with the acid used by removal of the reaction solvent, or in the free form by neutralization with a base followed by filtration or extraction.

The solvent for extraction includes halogenated hydrocarbons such as dichloromethan and chlorobenzene, aromatic hydrocarbons such as toluene and xylene, ethers such as diethyl ether, esters such as ethyl acetate, aliphatic hydrocarbons such as hexane and heptane, that is, non-water solubles solvent can be used without limit.

Method (b)

A mixture of hydrazines of the general formulae (1) and (2) is heated and stirred in the presence of an alcohol and an acid as a catalyst, and accordingly a carboxylic ester of the general formula (3) is formed from the 1-acyl-1-substituted hydrazine of the general formula (2) by alcoholysis. The 1-acyl-2-substituted hydrazine of the general formula (1) can be purified by removal of the carboxylic ester of the general formula (3).

In this method, mixtures containing various proportions of hydrazines of the general formulae (1) and (2) can be applied.

The alcohols as reaction solvent may include aliphatic alcohols, such as methanol, ethanol, n-propanol, isopropanol, n-butanol, iso-butanol and n-hexanol, preferably for example methanol, ethanol and isopropanol. The amount of the alcohol may be the theoretical or a large excess thereof. As the reaction solvents, organic solvents other than the alcohols may optionally and additionally be used. The additional solvent may include aliphatic hydrocarbons, such as hexane and heptane, aromatic hydrocarbons, such as benzene, toluene and xylene, halogenated hydrocarbons, such as chloroform, dichloromethane, chlorobenzene, ethers, such as diethyl ether and tetrahydrofuran, ketones, such as acetone and methyl ethyl ketone, and water. The total amount of the reaction solvent, that is, the amount of the alcohol and the optionally additional solvent may be not more than 10 L, preferably 0.5 to 5 L, per mole of the hydrazine mixture to be purified.

The acid catalyst may include inorganic acids, such as hydrochloric acid, sulfuric acid and nitric acid, and organic acids, such as p-toluenesulfonic acid. The preferable acid may be an inorganic acid and more preferable one is hydrochloric acid or sulfuric acid. The concentration of the acid used as a catalyst may be usually not more than 50% by weight, preferably not more than 30% by weight, most preferably 1 to 5% by weight, relative to the reaction solvent used.

The reaction temperatures may range from 10° C. to the boiling point of the reaction solvent used, preferably from about 50° C. to about 100° C.

The 1 acyl-2-substituted hydrazine of the general formula (1) can be obtained in the form of salt with the acid used, by filtration. After the separation of the hydrazine of the general formula (1), the carboxylic ester of the general formula (3) can be recovered by evaporation of the reaction solvent.

Examples of the substituent on the Ar of the compound represented by the formula (1) may include halogens, such as fluorine, chlorine, bromine and iodine, alkyl groups including those with a straight chain, such as methyl, ethyl, n-propyl and n-butyl, and those with a branched chain, such as i-propyl, i-butyl, t-butyl and sec-butyl, alkoxy groups including methoxy, ethoxy, n-propoxy, i-propoxy, n-butoxy and t-butoxy, haloalkyl groups including fluoromethyl, chloromethyl, bromomethyl, trifluoromethyl and 4-chlorobutyl, and haloalkoxy groups including fluoromethoxy, trifluoromethoxy, chloromethoxy and 2-fluoro-1,1-dimethyl-ethoxy. The preferable substituent on the phenyl group of Ar may be selected from the groups consisting of hydrogen, halogens, and $(C_1-C_6)$alkyl groups. The preferable Ar group may include one wherein the two adjacent substituents on the phenyl ring form —OCH$_2$CH$_2$O— or —OCH$_2$CH$_2$CH$_2$—, and phenyl group having an ethyl group at 4-position thereof. Another preferable Ar may be 5-methyl-6-chromanyl or 5-methyl-1,4-benzodioxane-6-yl. The preferable $R^1$ group may be a tertiary-alkyl group and more preferable one may be t-butyl and the preferable $R^2$ group may be hydrogen, methyl, ethyl or isopropyl.

[EXAMPLES]

The invention is further illustrated by, but is not limited to, the following Examples. In Examples, the percentages represent those by weight.

Example 1

Purification of 1-(5-methylchroman-6-carbonyl)-2-t-butyl hydrazine [Method (a); Acid: Hydrochloric Acid]

To a mixture of 57.8 g of a solid containing 80% of 1-(5-methylchroman-6-carbonyl)-2-t-butyl hydrazine and 20% of 1-(5-methylchroman-6-carbonyl)-1-t-butyl hydrazine and 900 ml of water was added 100 ml of concentrated hydrochloric acid at room temperature and then the the resultant was heated under reflux for 30 minutes. After cooling with ice and water, the resulting crystals were filtered to obtain 7.11 g of 5-methyl-6-chromanic acid in a yield of 16.8% (which had a purity of 99.5% by peak area from HPLC analysis and a melting point of 207° to 208° C.). An 50% aqueous solution of sodium hydroxide was added to the filtrate to pH 8 followed by extraction with dichloromethane to obtain 45.8 g of 1-(5-methylchroman-6-carbonyl)-2-t-butyl hydrazine in a yield of 79.1% (which had a purity of 99.8% by peak area from HPLC analysis and a melting point of 146° to 148° C. while which contained not more than 0.1% by peak area of 1-(5-methylchroman-6-carbonyl)-1-t-butyl hydrazine from HPLC analysis).

Example 2

Purification of 1-(5-methylchroman-6-carbonyl)-2-t-butyl hydrazine [Method (a); Acid: Sulfuric Acid]

To a mixture of 2.0 g of a mixture containing 88.1% of 1-(5-methylchroman-6-carbonyl)-2-t-butyl hydrazine and 5.8% of 1-(5-methylchroman-6-carbonyl)-1-t-butyl hydrazine and 9.1 ml of water was added 1.2 g of concentrated sulfuric acid at room temperature and then the resultant was heated under reflux for 1 hour. After cooling with ice and water, the resulting crystals were filtered off. An 50% aqueous solution of sodium hydroxide Was added to the filtrate to the aqueous phase to an alkaline pH value followed by extraction with dichloromethane to obtain 1.67 g of 1-(5-methylchroman-6-carbonyl)-2-t-butyl hydrazine in a yield of 83.5% (which had a purity of 96.7% by peak area while which contained not more than 0.1% by peak area of 1-(5-methylchroman-6-carbonyl)-1-t-butyl hydrazine from HPLC analysis).

Example 3

Preparation of 1-(5-methylchroman-6-carbonyl)-2-t-butyl hydrazine

Step 1: Monobenzoylation

To a mixture containing 51.2 g of sodium hydroxide, 205 ml of water, 92.0 g of t-butyl hydrazine hydrochloride and 393 ml of methylene chloride was dropwise added 5-methylchroman-6-carboxylic chloride over 30 minutes at a temperature of −10° to −2° C. The reaction mixture was warmed to room temperature and stirred for 2 hours. The methylene chloride phase was separated, washed with 5% brine. The phase was concentrated under vacuum to obtain 136.77 g of a pale yellowish solid. The solid contained 88.4% of 1-(5-methylchroman-6-carbonyl)-2-t-butyl hydrazine and 4.0% by peak area of 1-(5-methylchroman-6-carbonyl)-1-t-butyl hydrazine from HPLC analysis.

Step 2: Acid Treatment [Method (a); Acid: Hydrochloric Acid]

To a mixture of the resulting solid and 738 ml of water was added 103 g of concentrated hydrochloric acid at room temperature and the resultant was heated under reflux for 3 hours. The reaction mixture was cooled to 10° C. and then the precipitated crystals were filtered. The crystals were washed two times with water to obtain 6.52 g of 5-methylchroman-6-carboxylic acid with a purity of 92.1%. Methylene chloride was added to the filtrate and then, with stirring and cooling, an 50% aqueous solution of sodium hydroxide was added to the aqueous phase to an alkaline pH value. The methylene chloride phase was separated washed with 5% brine, dried with magnesium sulfate and filtered followed by concentration thereof to obtain 117.8 g of 1-(5-methylchroman-6-carbonyl)-2-t-butyl hydrazine with a purity of 91.5%.

Example 4

Preparation of 1-(4-ethylbenzoyl)-2-t-butyl hydrazine

Step 1: Monobenzoylation

To a mixture containing 2.73 g of sodium hydroxide, 10.9 g of water, 4.44 g of t-butylhydrazine hydrochloride and 24 ml of methylene chloride was dropwise added 4-ethylbenzoyl chloride over 20 minutes at a temperature of −10° to 0° C. The reaction mixture was warmed to room temperature and stirred for 1 hours. The methylene chloride phase was separated, washed two times with water. The phase was dried over magnesium sulfate and filtered followed by concentration to obtain a pale yellowish solid, which contained 90.8% of 1-(4-ethylbenzoyl)-2-t-butyl hydrazine and 7.68% of 1-(4-ethylbenzoyl)-1-t-butyl hydrazine.

Step 2: Acid Treatment [Method (a); Acid: Hydrochloric Acid]

To a mixture of the resulting solid and 36 ml of water was added 9.3 g of concentrated hydrochloric acid at room temperature and the resultant was heated under reflux for 30 minutes. The reaction mixture was cooled to 10° C. and then the precipitated crystals were filtered. The crystals were washed with 15 ml of water three times to obtain 1.02 g of 4-ethyl benzoic acid (88.7% by peak area from HPLC analysis).

Methylene chloride was added to the filtrate and then, with stirring and cooling, an 50% aqueous solution of sodium hydroxide was added to the aqueous phase to an alkaline pH value. The methylene chloride phase was separated, washed two times with water, dried with magnesium sulfate and filtered followed by concentration thereof to obtain 5.10 g of 1-(4-ethylbenzoyl)-2-t-butyl hydrazine with a purity of 99.4% in a yield of 77.8% as a white crystal, which did not substantially contain 1-(4-ethylbenzoyl)-1-t-butyl hydrazine (which contained not more than 0.02% of it).

Example 5

Purification of 1-(5-methylchroman-6-carbonyl)-2-t-butyl hydrazine [Method (b); Acid: Hydrochloric Acid]

To a solid consisting of 70% of 1-(5-methylchroman-6-carbonyl)-2-t-butyl hydrazine and 30% of 1-(5-methylchroman-6-carbonyl)-1-t-butyl hydrazine was added 10 ml of dehydrated ethanol containing 10% of hydrochloric acid and then the resultant was heated under reflux for 30 minutes. After cooling with ice and water, the precipitated crystals were filtered to obtain 0.88 g of 1-(5-methylchroman-6-carbonyl)-2-t-butyl hydrazine hydrochloride with a melting point of 217° to 220° C. in a yield of 68%. The filtrate was concentrated to obtain 0.25 g of ethyl methylchromanate with a melting point of 79° to 80° C. in a yield of 29%.

Examples 6 to 8

Hydrazine compounds listed in Table 1 below were purified by the procedures as described in Examples 1, 2, 3 and 4.

The analytical data of the products obtained are illustrated in Table 1.

TABLE 1

Conditions of Acid Treatment and Analytical Data

| | | | | | Before Acid Treatment | | | After Acid Treatment | | |
|---|---|---|---|---|---|---|---|---|---|---|
| Example | Ar | $R^1$ | $R^2$ | Method (Acid) | Weight (g) | Content of Compound (1)* | Content of Compound (2)* | Weight (g) | Content of Compound (1)* | Content of Compound (2)* |
| 1 | 5-methyl-6-chromanyl | t-butyl | H | a (HCl) | 57.8 | 80 W % | 20 W % | 45.8 | 99.8 S % | <0.1 S % |
| 2 | 5-methyl-6-chromanyl | t-butyl | H | a ($H_2SO_4$) | 20 | 88.1 W % | 5.8 W % | 1.67 | 96.7 S % | <0.1 S % |
| 3 | 5-methyl-6-chromanyl | t-butyl | H | (HCl) (HCl) | 136.77 | 88.4 W % | 4.0 S % | 117.8 | 91.5 W % | <0.1 S % |
| 4 | 4-ethyl phenyl | t-butyl | H | a (HCl) | 6.5 | 90.8 W % | 7.68 W % | 5.10 | 99.4 W % | <0.02 W % |
| 5 | 5-methyl-6-chromanyl | t-butyl | Et | b (HCl) | 1.00 | 70 W % / 85 S % | 30 W % / 15 S % | 0.88 | 98.9 S % | <0.1 S % |
| 6 | phenyl | t-butyl | H | a (HCl) | 3.00 | 70.7 S % | 5.9 S % | 2.20 | 95.7 S % | 0.1 S % |
| 7 | 5-methyl-1,4-dioxane-6-yl | t-butyl | H | a (HCl) | 2.42 | 92.4 S % | 3.6 S % | 2.28 | 93.5 S % | <0.1 S % |
| 8 | 4-chlorophenyl | t-butyl | H | a ($H_2SO_4$) | 3.00 | 96.6 S % | 2.6 S % | 2.59 | 99.6 S % | <0.03 S % |

W %: quantitative % by weight, S %: % by peak area in HPLC

[Advantageous Effects of Invention]

According to the invention, 1-acyl-2-alkyl hydrazines being usable intermediates for the production of 1-alkyl-1,2-diacyl hydrazines which are known to have insecticidal activities, can be prepared in high purities.

In addition, carboxylic acids or esters thereof derived from the impurity, 1-acyl-1-alkyl hydrazines according to the invention can be reused as starting materials for the preparation of the desired 1-acyl-2-alkyl hydrazine.

What is claimed is:

1. A process for separating a 1-acyl-2-substituted hydrazine compound represented by the formula (1):

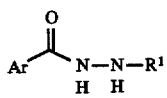 (1)

wherein Ar is a phenyl or naphthyl group substituted by 1 to 5 substituents independently selected from the group consisting of hydrogen, halogen, $(C_1-C_6)$alkyl, $(C_1-C_6)$alkoxy, halo$(C_1-C_6)$alkyl and halo$(C_1-C_6)$alkoxy, or when two adjacent positions on the phenyl ring are substituted, these groups can form —OCH$_2$CH$_2$O— or —OCH$_2$CH$_2$CH$_2$—, and $R^1$ is a $(C_1-C_6)$alkyl group, from a mixture of said hydrazine compound and a 1-acyl-1-substituted hydrazine represented by the formula (2):

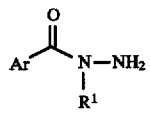 (2)

wherein Ar and $R^1$ are as described above, said process comprising the following steps of: deriving a compound represented by the formula (3):

 (3)

wherein Ar is as described above and $R^2$ is hydrogen or a $(C_1-C_6)$alkyl, from the 1-acyl-1-substituted hydrazine of the formula (2) by selective hydrolysis in the presence of an acid catalyst, or by selective alcoholysis in the presence of an acid catalyst; and separating said derived compound represented by the formula (3) from said 1-acyl-2-substituted hydrazine compound represented by the formula (1).

2. The process according to claim 1, wherein the substituent(s) on the phenyl group of Ar are selected from the group consisting of hydrogen, halogen and $(C_1-C_6)$ alkyl.

3. The process according to claim 2, wherein Ar is 4-ethylphenyl.

4. The process according to claim 1, wherein the adjacent two substituents on the phenyl ring of Ar is —OCH$_2$CH$_2$O— or —OCH$_2$CH$_2$CH$_2$—.

5. The process according to claim 4, wherein Ar is 5-methyl-6-chromanyl.

6. The process according to claim 4, wherein Ar is 5-methyl-1,4-benzodioxane-6-yl.

7. The process according to claim 1, 2, 3, 4, 5 or 6, wherein $R^1$ is a tertiary alkyl group.

8. The process according to claim 7, wherein $R^1$ is tertiary butyl.

9. The process according to claim 7, wherein $R^2$ is hydrogen, methyl, ethyl or isopropyl.

10. The process according to claim 7, wherein the acid catalyst is an inorganic acid.

11. The process according to claim 10, wherein the acid catalyst is hydrochloric acid or sulfuric acid.

12. The process according to claim 11, wherein the hydrolysis is carried out using water or a mixture of water and an organic solvent as a reaction solvent.

13. The process according to claim 11, wherein the hydrolysis is carried out using water or a mixture of water and methanol, of water and ethanol or of water and isopropanol as a reaction solvent.

14. The process according to claim 13, wherein the hydrolysis is carried out in the presence of water and an acid catalyst.

15. The process according to claim 10, wherein the alcoholysis is carried out using methanol, ethanol or isopropanol as a reaction solvent.

16. The process according to claim 10, wherein the hydrolysis or alcoholysis is carried out at temperatures of 50° to 100° C.

* * * * *